(12) United States Patent
Kubota

(10) Patent No.: US 11,636,934 B2
(45) Date of Patent: Apr. 25, 2023

(54) STORAGE MEDIUM, MEDICAL INFORMATION PROCESSING DEVICE, AND MEDICAL INFORMATION PROCESSING METHOD

(71) Applicant: KONICA MINOLTA, INC., Tokyo (JP)

(72) Inventor: Hiroyuki Kubota, Kunitachi (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 17/159,277

(22) Filed: Jan. 27, 2021

(65) Prior Publication Data
US 2021/0241870 A1    Aug. 5, 2021

(30) Foreign Application Priority Data

Jan. 31, 2020 (JP) .............................. JP2020-014374

(51) Int. Cl.
| | |
|---|---|
| H03M 7/00 | (2006.01) |
| G16H 15/00 | (2018.01) |
| G06F 40/20 | (2020.01) |
| G06F 40/126 | (2020.01) |

(52) U.S. Cl.
CPC ........... *G16H 15/00* (2018.01); *G06F 40/126* (2020.01); *G06F 40/20* (2020.01); *H03M 7/00* (2013.01)

(58) Field of Classification Search
CPC ........ G16H 15/00; G06F 40/126; G06F 40/20
See application file for complete search history.

(56) References Cited

U.S. PATENT DOCUMENTS

| | | | | |
|---|---|---|---|---|
| 6,049,869 A | * | 4/2000 | Pickhardt | G06F 16/90344 715/264 |
| 2002/0016922 A1 | * | 2/2002 | Richards | H04L 63/0428 726/3 |
| 2011/0157634 A1 | * | 6/2011 | Shibata | G06F 40/151 358/1.15 |
| 2011/0211762 A1 | | 9/2011 | Carter et al. | |
| 2013/0176589 A1 | * | 7/2013 | Nakamura | G06F 3/1288 358/1.15 |
| 2015/0095016 A1 | * | 4/2015 | Karres | G16H 10/60 704/9 |

(Continued)

FOREIGN PATENT DOCUMENTS

JP    2006004192 A    1/2006

OTHER PUBLICATIONS

U.S. Appl. No. 17/155,213; First Named Inventor: Hiroyuki Kubota; Title: "Storage Medium, Medical Information Processing Device, and Medical Information Processing Method"; Filed: Jan. 22, 2021.

(Continued)

*Primary Examiner* — Xuyang Xia
(74) *Attorney, Agent, or Firm* — Holtz, Holtz & Volek PC

(57) ABSTRACT

Provided is a non-transitory storage medium that stores a computer readable program for a computer of a medical information processing device configured to output and/or input medical information, the program causing the computer to perform acquiring locale information in environment information of the medical information processing device and presuming a character encoding of the medical information based on the locale information acquired in the acquiring.

9 Claims, 5 Drawing Sheets

(56) References Cited

U.S. PATENT DOCUMENTS

2015/0097701 A1 4/2015 Al-Ali et al.
2016/0378722 A1* 12/2016 Emmons ............... G06F 40/126
　　　　　　　　　　　　　　　　　　345/472.3

OTHER PUBLICATIONS

Office Action (Non-Final Rejection) dated Jan. 31, 2023, issued in related U.S. Appl. No. 17/155,213.

* cited by examiner

| LOCALE INFORMATION | LANGUAGE | COUNTRY/REGION |
|---|---|---|
| zh_CN | CHINESE | CHINA |
| zh_HK | CHINESE | HONG-KONG |
| en_GB | ENGLISH | UK |
| en_US | ENGLISH | US |
| fr_CA | FRENCH | CANADA |
| fr_FR | FRENCH | FRANCE |
| de_DE | GERMAN | GERMANY |
| de_CH | GERMAN | SWITZERLAND |
| ja_JP | JAPANESE | JAPAN |
| pt_BR | PORTUGUESE | BRAZIL |
| pt_PT | PORTUGUESE | PORTUGAL |

STORAGE MEDIUM, MEDICAL INFORMATION PROCESSING DEVICE, AND MEDICAL INFORMATION PROCESSING METHOD

CROSS-REFERENCE TO RELATED APPLICATIONS

The entire disclosure of Japanese Patent Application No. 2020-014374 filed on Jan. 31, 2020 is incorporated herein by reference in its entirety.

BACKGROUND

Technological Field

The present invention relates to a storage medium, a medical information processing device, and a medical information processing method.

Description of the Related Art

Generation of medical information in imaging apparatuses, report systems, ordering systems, etc. and exchange of medical information between devices are carried out in conformity with a medical data standard such as Digital Imaging and Communications in Medicine (DICOM), and Health Level Seven International (HL7).

Such medical data standards support character encodings suitable for countries and regions where the devices are used. For example, ASCII is used in the U.S., Latin 1 in France, Europe, Latin 4 in Sweden, also Europe, and JIS for half-width kana, JIS for commonly-used kanji, etc. in Japan.

A character encoding declaration by a device that transmits medical information enables a device that receives the information (destination) to process the encoding in the received information so that the information is output correctly.

However, ASCII does not require the character encoding declaration exceptionally among many encodings, because of its development history. As a result, in some cases, the encoding declaration is omitted by mistake in transmission of medical information that uses an encoding other than ASCII. When a device receives such medical information (destination), the device outputs the medical information in ASCII, the user cannot recognize the output medical information.

In order to deal with such a problem, identification information of a client that receives medical information and a character type(s) that can be recognized by the client are registered beforehand in a server that transmits the medical information, and when the server transmits the medical information, the server refers to the registered identification information and declares the encoding suitable for the client that receives the medical information (for example, see JP2006-004192A).

SUMMARY

However, the technique disclosed in JP2006-004192A cannot deal with the problem in a case where the server declares an encoding inconsistent with the encoding actually used for the medical information.

Also, in a case where the destination device to be registered beforehand has no specifications published or no maintenance provided, the encoding suitable for the destination device cannot be confirmed, and pre-registration may be difficult.

Further, in a case where medical information is exchanged via a medium, a client(s) and character types cannot be registered beforehand, and an appropriate encoding declaration is impossible.

Especially when medical information including characters of a single encoding is exchanged using JP2006-004192A, the medical information does not include an escape sequence as a clue for identifying the encoding, making it difficult to identify the encoding.

The present invention has been conceived in view of such problems, and has an object of enabling interpretation of medical information with characters of a single encoding in cases where an encoding declaration by a device that transmits medical information is incorrect or where an encoding for a device that receives information is not registered beforehand.

To achieve at least one of the abovementioned objects, according to an aspect of the present invention, a non-transitory storage medium reflecting one aspect of the present invention stores a computer readable program for a computer of a medical information processing device configured to output and/or input medical information, the program causing the computer to perform:

acquiring locale information in environment information of the medical information processing device; and presuming a character encoding of the medical information based on the locale information acquired in the acquiring.

To achieve at least one of the abovementioned objects, according to another aspect of the present invention, a medical information processing device reflecting one aspect of the present invention includes:

an acquirer that acquires locale information in environment information of the medical information processing device; and a presumption unit that presumes a character encoding of medical information input and/or output by the medical information processing device based on the locale information acquired by the acquirer.

To achieve at least one of the abovementioned objects, according to another aspect of the present invention, a medical information processing method reflecting one aspect of the present invention includes:

acquiring locale information in environment information of a medical information processing device; and presuming a character encoding of medical information input and/or output by the medical information processing device based on the locale information acquired in the acquiring.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, an embodiment of the present invention is described with reference to the drawings. However, the scope of the present invention is not limited to the embodiments or illustrated examples.

[1. Medical Information Processing System]

First, a schematic configuration of a medical information processing system 100 in this embodiment is described.

Figure 1:
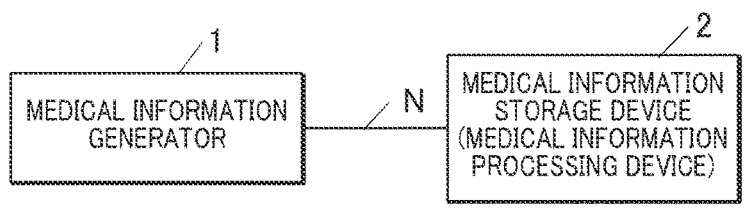
FIG. 1 is a block diagram showing a medical information processing system in an embodiment of the present invention.

FIG. 1 is a block diagram showing the medical information processing system 100.

The medical information processing system 100 includes a medical information generator 1 and a medical information storage 2.

The medical information generator 1 and the medical information storage 2 can communicate with each other via a communication network N.

The communication network N may be wired or wireless.

The medical information generator 1 and the medical information storage 2 may exchange information using a recording medium (a USB memory, DVD-ROM, etc.) without the communication network N.

The medical information generator 1 in this embodiment is, for example, an imaging apparatus that generates medical images, a report system for creating reports, or an ordering system for entering order information.

The medical information generator 1 may generate digital content for medical use.

The "digital content" is text or audiovisual representations of images, figures, audio, video, in the form of digital data expressed by combinations of 0 and 1 in some data format.

For example, audio stored in a storage medium (CD-ROM, etc.) is a kind of the digital content.

The digital content includes computer programs that display/play such content or change it according to the user operation, such as video games.

The digital content may be directly stored or processed in computers, and is easily modified, copied, and transmitted. Moreover, it is less likely to deteriorate due to the state of the recording medium or transmission medium.

The digital content handled by the medical information processing system 100 in this embodiment is at least any of patient information in HL7, order information in HL7, DICOM images (medical images), and DICOM structured documents (reports, etc.).

The digital content includes medical information.

"Medical information," which is information related to medical practice, specifically includes image information, report information, patient information, order information, clinical test result information, insurance claim information, clinical records, and radiation dose information.

The medical information storage 2 in this embodiment is, for example, a server, or a terminal device.

The medical information storage 2 may store digital content generated by the medical information generator 1.

The medical information storage 2 in this embodiment also functions as a medical information processing device.

The medical information storage 2 is described in detail later.

Figure 2:
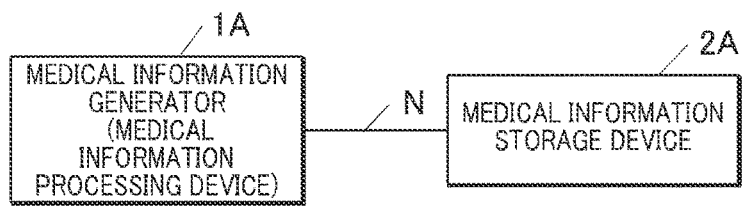
FIG. 2 is a block diagram showing a medical information processing system in a variation of the present invention.

In FIG. 1, the medical information storage 2 (a computer that can execute input (reception) of medical information) also functions as the medical information processing device, but as shown in FIG. 2, the medical information generator 1A (a computer that can execute output (transmission) of medical information) may also function as the medical information processing device.

Figure 3:
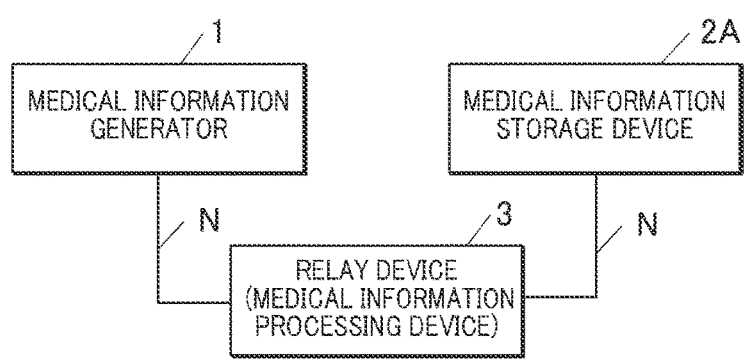
FIG. 3 is a block diagram showing a medical information processing system in another variation of the present invention.

Alternatively, as shown in FIG. 3, the medical information generator 1 and the medical information storage 2A may be separately provided, and a relay device (a computer that can execute input and output (transfer) of medical information) between the medical information generator 1 and the medical information storage 2A may be provided for communication between the medical information generator 1 and the medical information storage 2A so as to function as the medical information processing device.

[2. Medical Information Processing Device]

Next, the medical information storage 2 of the medical information processing system 100, as an example of the medical information processing device, is described in detail.

Figure 4:
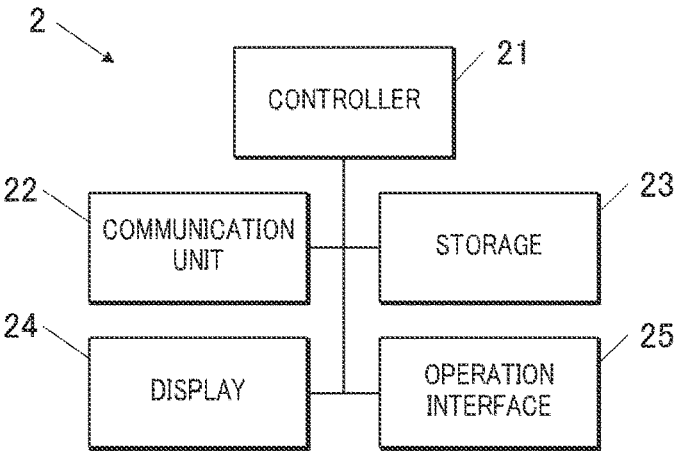
FIG. 4 is a block diagram showing a medical information processing device of the medical information processing system in FIG. 1, 2, or 3.
Figure 5:
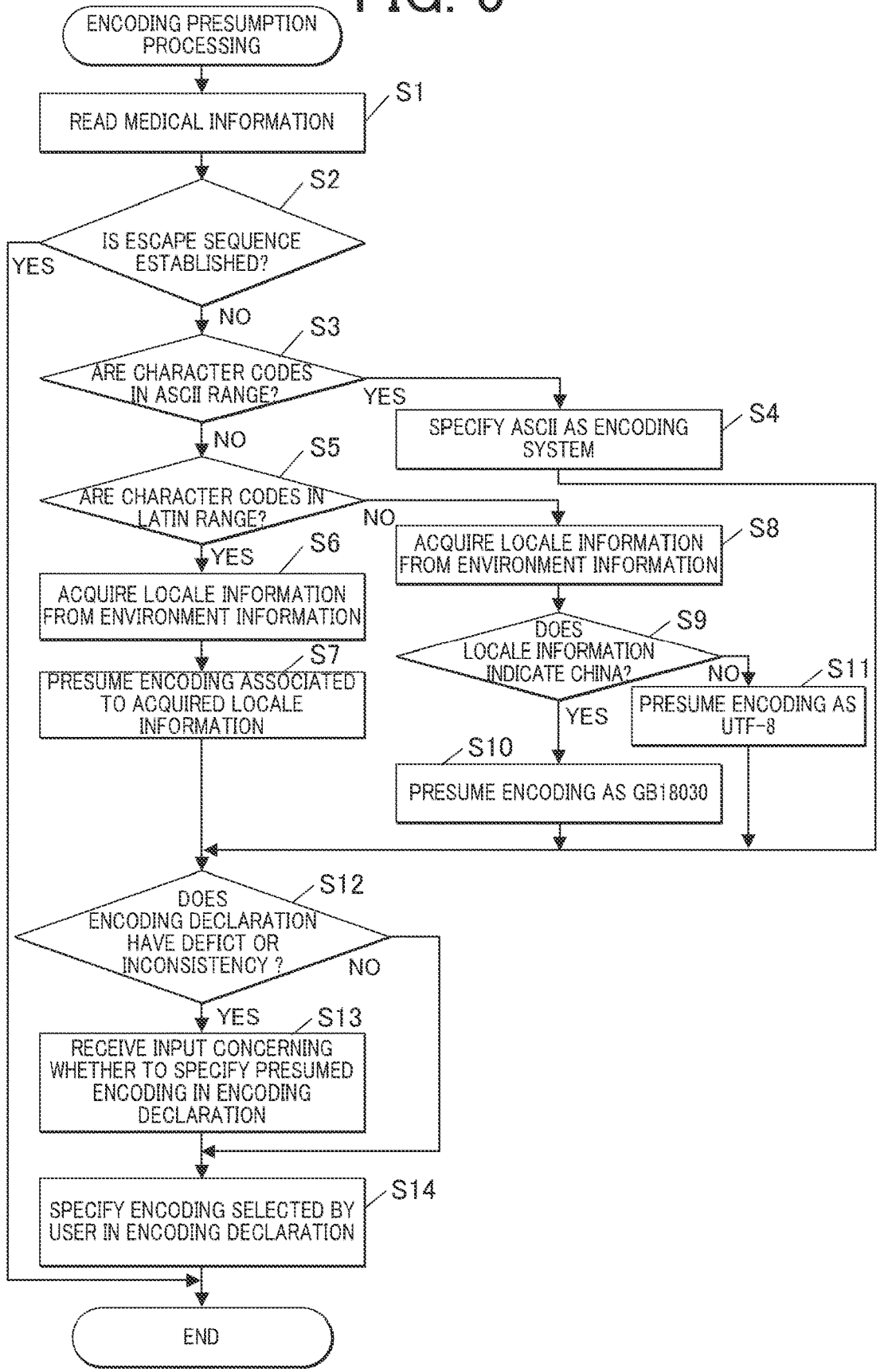
FIG. 5 shows an example of a flowchart of steps of encoding presumption processing executed by the medical information processing device in FIG. 4.

FIG. 4 is a block diagram of the medical information processing device, and FIG. 5 is a flowchart showing steps of encoding presumption processing executed by the medical information processing device.

As described above, the medical information processing device may be the medical information generator 1A or the relay device 3.

(Configuration of Medical Information Processing Device)

The medical information storage 2 includes a controller 21, a communication unit 22, and a memory 23.

The medical information storage 2 in this embodiment further includes a display 24 and an operation interface 25.

The controller 21 includes, for example, a central processing unit (CPU) and a random access memory (RAM).

The CPU of the controller 21 reads out various programs (including a program for executing the encoding presumption processing described later) stored in the memory 23, deploys them in the RAM, and executes various kinds of processing according to the deployed programs to centrally control the operation of the components of the medical information storage 2.

The communication unit 22, which includes, for example, a wired communication module and a wireless communication module, may send and receive various signals and various kinds of data (including medical information) to and from other devices (the medical information generator 1, the medical information storage 2, etc.) connected via the communication network N (LAN, WAN, Internet, etc.) wirelessly or by wire.

The medical information storage 2 may include a reading/writing unit that can read and write information on a recording medium instead of the communication unit 22.

The memory 23 includes, for example, a non-volatile semiconductor memory, and a hard disk.

The memory 23 stores programs for execution of the processing by the controller 21, parameters necessary for execution of the programs, etc.

The memory 23 in this embodiment may store image data of radiographs.

The medical information storage 2 includes an image data memory provided independently from the memory 23.

The display 24, which is composed of a monitor including a liquid crystal display (LCD) and a cathode ray tube, displays various images, various kinds of information, etc. according to commands of display signals input from the controller 21.

The operation interface 25 includes a keyboard with cursor keys, number keys, and various function keys, a pointing device such as a mouse, and a touch panel superimposed on the surface of the display 24, and is operable by the user.

The operation interface 25 outputs control signals based on the operation by the user to the controller 21.

In the medical information processing system 100, 100A, or 100B including a terminal device (for example, a tablet terminal) with a display, an operation interface, etc. beside the medical information processing device, the medical information storage 2 may not include the display 24 or the operation interface 25.

(Operation of Medical Information Processing Device)

The controller 21 of the medical information storage 2 configured as described above has a function of executing the encoding presumption processing shown in FIG. 5, triggered by acquisition of medical information from other devices (the medical information generator 1, etc.), input of a predetermined operation on the operation interface 25, etc.

In the encoding presumption processing, the controller 21 first executes a reading step (Step S1).

In the reading step, the controller 21 reads all the characters in medical information acquired from other devices.

After reading the medical information, the controller 21 in this embodiment executes a determination step (Step S2).

At the determination step, the controller 21 determines whether or not the escape sequence is established in the medical information read at the reading step in this embodiment.

The "escape sequence" represents a character string that commands control of character output.

More specifically, the escape sequence is not a series of literal characters to be output, but is a special character string that commands change of the character encoding, change of character colors, cursor motion, character deletion, etc. at the time of output of characters (to be displayed on the display 24, for example).

The controller 21 determines whether or not "ESC" and following characters indicating some encoding are present in the character string in the medical information in the determination step.

The "encoding" is a rule and standard for adding a character code to characters.

The character code includes, for example, ASCII (alphabets/numbers/symbols), Latin 1 (alphabets/western European characters/numbers/symbols), Latin 4 (alphabets/northern European characters/numbers/symbols), JIS for half-width kana (alphabets/symbols/symbols), JIS half-width (alphabets/half-width kanas/numbers/symbols), and JIS for commonly-used kanji (first and second level kanjis).

The controller 21 functions as a determination unit by execution of the determination step (Step S2).

The execution of the determination step corresponds to "determining" in the medical information processing method.

The controller 21 executes the reading step and the determination step alternately character by character.

If the controller 21 determines that an escape sequence is established in the read medical information (characters of different encodings exist in the medical information) in this determination step (Step S2: YES), the controller 21 ends the encoding presumption processing.

If an escape sequence is established in the medical information, the controller 21 may identify an encoding after being switched.

On the contrary, if the controller 21 determines that an escape sequence is not established in the read medical information (characters in the medical information have a common encoding) in the determination step (Step S2: NO), the controller 21 in this embodiment executes an exclusion step (Steps S3 to S5).

In this exclusion step, the controller 21 excludes an encoding(s) impossible for the encoding of the medical information from the encoding options based on the range of character codes used in the medical information.

The controller 21 in this embodiment determines whether or not the character codes of the characters included in the medical information are all in the range of ASCII (Step S3).

Specifically, the controller 21 determines whether or not the used character codes are those used for ASCII ("00" to "7F") only.

If the controller 21 determines that the character codes of the characters in the medical information are all included in the range of ASCII at Step S3 (Step S3: YES), the controller determines that the encoding is ASCII (excludes all the encodings beside ASCII as impossible) (Step S4), and ends the encoding presumption processing.

On contrary, if the controller 21 determines that at least part of the character codes of the characters in the medical information are not in the range of ASCII at Step S3 (Step S3: NO), the controller 21 determines whether or not the character codes of the characters in the medical information are all included in the range of Latin or half-width kana (Step S5).

Specifically, the controller 21 determines whether or not the used character codes include the character codes not used in Latin 1 to 15 or half-width kana.

If the controller 21 determines that the character codes of the characters in the medical information are all in the range of Latin or half-width kana at Step S5 (Step S5: YES), the controller 21 executes an acquisition step (Step S6).

As Step S5 is executed after the determination step (Step S2), the controller 21 executes the acquisition step if an escape sequence is not established.

Here, the encodings beside Latin 1 to 15 are excluded as impossible for the encoding of the medical information.

At the acquisition step, the controller 21 acquires locale information from environment information of the medical information processing device.

The "environment information" is information set by OS or applications.

Figures 6, 7:
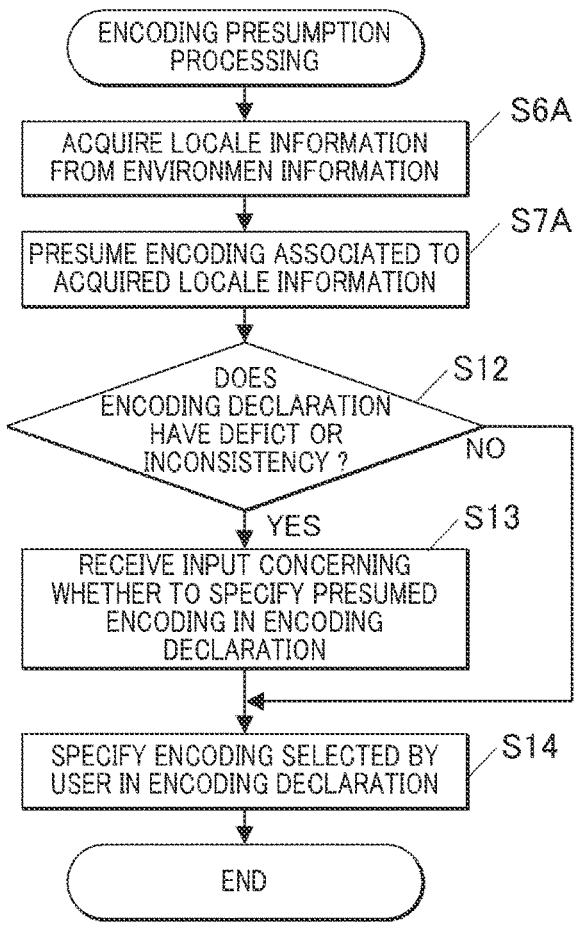
FIG. 6 is a table showing types of locale information.
FIG. 7 shows another example of a flowchart of steps of the encoding presumption processing executed by the medical information processing device in FIG. 4.

The "locale information" is information set by OS or applications, and includes a language code and a country/region code, as shown in FIG. 6. The unit and time in the locale information is different between English US (en_us) and English_GB (en_gb), for example, and the setting may be changed not only by OS, but also by application such as a browser.

The controller 21 functions as an acquirer by execution of the acquisition step (Step S6).

The execution of the acquisition step corresponds to "acquiring" in the medical information processing method.

The controller 21 executes a presumption step (Step S7) after the acquisition step as shown in FIG. 5, and proceeds to Step S12.

As Step S7 is executed after the determination step (Step S2), the controller 21 executes the presumption step if an escape sequence is not established.

At the presumption step, the controller 21 presumes the encoding of the medical information which is input and/or output to/from the medical information processing device based on the locale information acquired at the acquisition step.

Specifically, the country/region code included in the acquired locale information indicates France, the controller 21 presumes the encoding as Latin 1, and the country/region code indicates Russia, the controller 21 presumes the encoding as Cyrillic (Latin 5). If the country/region code indicates Japan, the controller 21 presumes the encoding as half-width kana.

In the case where it is difficult to specify a single encoding for single locale information (country/region code), multiple encodings may be presumed.

If the controller 21 determines that the character codes of the characters in the medical information are not in the range of Latin at Step S5 described above (Step S5: NO), the controller 21 executes the acquisition step (Step S8).

Here, Latin 1 to 15 are excluded as impossible for the encoding of the medical information.

The controller 21 executes a presumption step (Steps S9 to S11) after the acquisition step.

At the presumption step, the controller 21 determines whether or not the country/region code included in the locale information indicates China (Step S9).

If the controller 21 determines that the country/region code indicates China at Step S9 described above (Step S9: YES), the controller 21 presumes the encoding as GB18030 (Step S10), and proceeds to Step S12.

On contrary, if the controller 21 determines that the country/region code does not indicate China at Step S9 described above (Step S9: NO), the controller 21 presumes the encoding as UTF-8 (Step S11), and proceeds to Step S12.

The controller 21 in this embodiment executes a determination step (Step S12) after the presumption step (Step S7 or Steps S9 to S11).

At the determination step, the controller 21 determines whether or not the encoding declaration of the medical information includes a deficit or an inconsistency with the presumption result (presumed encoding).

If the controller 21 determines that the encoding does not include a deficit or an inconsistency from the presumption result at the determination step (Step S12: NO), the controller 21 proceeds to Step S14.

On contrary, if the controller 21 determines that the encoding includes a deficit or an inconsistency with the presumption result at the determination step (Step S12: YES), the controller 21 executes a selection step (Step S13).

At the selection step, the controller 21 may receive selection by a user concerning whether or not the encoding presumed in the presumption step is to be specified in the encoding declaration.

Specifically, for example, a list of encodings presumed is shown on the display 24, and the user selects an encoding (whether or not the presumed encoding is applied, in the case where just one encoding is presumed) from the list using the operation interface 25.

If the controller 21 determines that the encoding does not include a deficit or an inconsistency with the presumption result at the determination step, or if the user inputs that the presumed encoding is specified in the encoding declaration, the controller 21 executes a specifying step (Step S14).

At the specifying step, the controller 21 specifies the encoding selected by the user in the encoding declaration.

(Variation 1)

In the above embodiment, the acquisition step (Steps S6, S8) is executed after the exclusion step (Steps S3 to S5). However, the controller 21 may start the encoding presumption processing from the acquisition step (Step S6A) as shown in FIG. 7.

(Variation 2)

Figure 8:
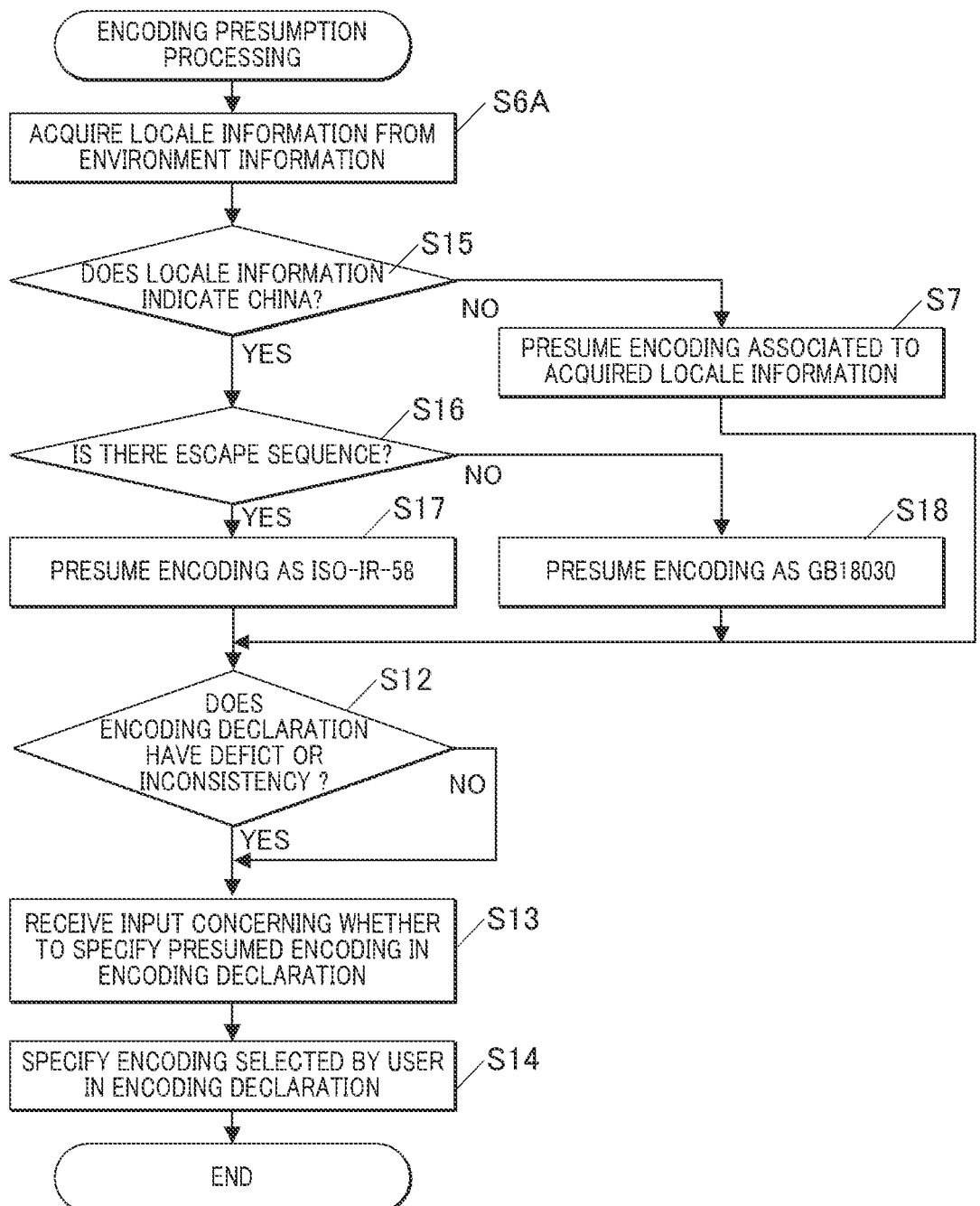
FIG. 8 shows another example of a flowchart of steps of the encoding presumption processing executed by the medical information processing device in FIG. 4.

The controller 21 may execute steps as shown in FIG. 8, for example, after the acquisition step (Step S6A).

Specifically, the controller 21 determines whether or not the country/region code included in the acquired locale information indicates China (Step S15).

If the controller 21 determines that the country/region code included in the acquired locale information indicates China (Step S15: YES), the controller 21 determines whether or not an escape sequence is included in the medical information (Step S16).

If the controller 21 determines that an escape sequence is included at Step S16 (Step S16: YES), the controller 21 presumes the encoding as ISO-IR-58 (Step S17).

On contrary, if the controller 21 determines that an escape sequence is not included at Step S16 (Step S16: NO), the controller 21 presumes the encoding as GBK or GB18030 (Step S18).

Figure 9:
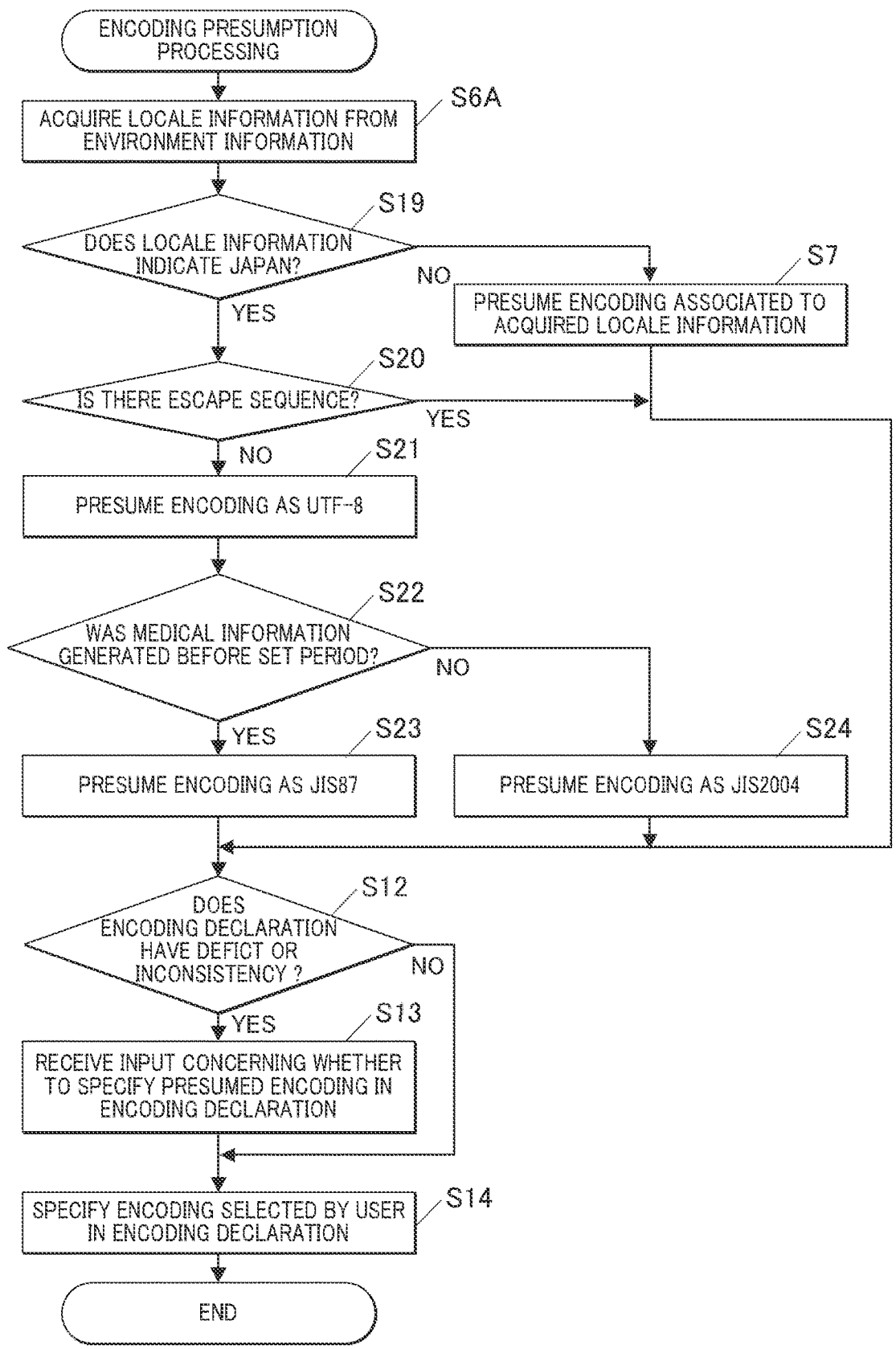
FIG. 9 shows another example of a flowchart of steps of the encoding presumption processing executed by the medical information processing device in FIG. 4.

(Variation 3),

The controller 21 may execute steps as shown in FIG. 9, for example, after the acquisition step (Step S6).

Specifically, the controller 21 determines whether or not the country/region code included in the acquired locale information indicates Japan (Step S19).

If the controller 21 determines that the country/region code indicates Japan at Step S19 (Step S19: YES), the controller 21 determines whether or not an escape sequence is included in the medical information (Step S20).

If the controller 21 determines that an escape sequence is included at Step S20 (Step S20: YES), the controller 21 proceeds to Step S12.

On contrary, if the controller 21 determines that an escape sequence is not included at Step S20 (Step S20: NO), the controller 21 presumes the encoding as UTF-8, and determines whether or not the medical information is generated before a predetermined period (for example, 2004) (Step S22).

If the controller 21 determines that the medical information is generated before the predetermined period at Step S22 (Step S22: YES), the controller 21 presumes the character set as one that was used before the predetermined period (for example, JIS90) (Step S23).

On contrary, if the controller 21 determines that the medical information is generated after the predetermined period at Step S22 (Step S22: NO), the controller 21 presumes the character set as one that is used after the predetermined period (for example, JIS2004) (Step S24).

[3. Effects]

The medical information processing device (medical information storage 2, medical information generator 1A, relay device 3) presumes the character encoding of the medical information based on the locale information of the medical information processing device. That is, the encoding is filtered without referring to an encoding declaration or escape sequence included in the medical information.

This makes it possible to interpret medical information with characters of a single encoding in cases where an encoding declaration by a device that transmits medical information is incorrect or where an encoding for a device that receives information is not registered beforehand, according to the embodiment of the medical information processing device.

[4. Misc.]

It is needless to mention that the present invention is not limited to the above embodiment and can be appropriately modified without departing from the scope of the present invention.

For example, in the above embodiment, the present invention is described as the medical information processing device of the medical information processing system 100, 100A, or 100B. However, the present invention may be applied to various devices and systems.

For example, the present invention may be applied to an imaging apparatus, an image server, an electronic clinical record, an RIS, a clinical examination department system, an image interpretation report system, a medical expense management computer, a gateway device, etc.

In the above embodiment, the encoding is presumed based on the country/region code included in the locale information. However, the encoding may be presumed based on the language code included in the locale information, the font information included in the OS or applications, etc.

Further, in the above description, a hard disk, a non-volatile semiconductor memory, etc. are used as a computer readable medium of the programs of the present invention, but the embodiments are not limited to this example. A portable recording medium such as a CD-ROM can be applied as other computer readable media.

A carrier wave is also applied as a medium providing the program data according to the present invention via a communication line.

What is claimed is:

1. A non-transitory storage medium having stored thereon a computer readable program that is executable by a computer of a medical information processing device configured to output and input medical information, the program being executable by the computer to cause the computer to perform:
   reading the medical information;
   determining whether an escape sequence for switching a character encoding is established in the medical information read in the reading, wherein the escape sequence is a special character string that commands at least one of change of the character encoding, change of character colors, cursor motion, and character deletion, at a time of output of characters of the medical information; and
   in response to a determination that the escape sequence for switching the character encoding is not established:
      acquiring locale information in environment information of the medical information processing device;
      searching, in a look-up table, a value mapped to by the locale information by using the locale information as a key, the value being associated with a character encoding;
      presuming a character encoding of the medical information based on a result of the searching; and
      decoding the input medical information based on the presumed character encoding.

2. The non-transitory storage medium according to claim 1, wherein the program further causes the computer to perform:
   determining whether an encoding declaration of the medical information includes a deficit or an inconsistency with the presumed encoding in the presuming; and
   in response to a determination that the encoding declaration includes the deficit or the inconsistency, receiving input of a user selection concerning whether the presumed character encoding is to be specified in the encoding declaration.

3. The non-transitory storage medium according to claim 2, wherein the program further causes the computer to perform:
   specifying the character encoding according to the user selection in the receiving in the encoding declaration.

4. The non-transitory storage medium according to claim 1, wherein the program further causes the computer to perform:
   excluding an encoding that is impossible as the encoding of the medical information from multiple encoding options for the presuming based on a range of character codes used in the medical information.

5. The non-transitory storage medium according to claim 1,
   wherein the medical information is included in at least one of:
   a medical image generated by an imaging apparatus;
   a report created in a report system; and
   order information generated by an ordering system.

6. A medical information processing device comprising:
   a hardware processor that is configured to:
   read the medical information;
   determine whether an escape sequence for switching a character encoding is established in the medical information read in the reading, wherein the escape sequence is a special character string that commands at least one of change of the character encoding, change of character colors, cursor motion, and character deletion, at a time of output of characters of the medical information; and
   in response to a determination that the escape sequence for switching the character encoding is not established:
      acquire locale information in environment information of the medical information processing device;
      search, in a look-up table, a value mapped to by the locale information by using the locale information as a key, the value being associated with a character encoding;
      presume a character encoding of the medical information based on a result of the searching; and
      decode the input medical information based on the presumed character encoding.

7. The medical information processing device according to claim 6, wherein the hardware processor is further configured to:
   determine whether an encoding declaration of the medical information includes a deficit or an inconsistency; and
   in response to a determination that the encoding declaration includes the deficit or the inconsistency, receive input of a user selection concerning whether the presumed character encoding is to be specified in the encoding declaration.

8. A medical information processing method comprising:
   reading the medical information;
   determining that an escape sequence for switching a character encoding is not established in the medical information read in the reading, wherein the escape sequence is a special character string that commands at least one of change of the character encoding, change of character colors, cursor motion, and character deletion, at a time of output of characters of the medical information; and in response to the determination that the escape sequence for switching the character encoding is not established:
acquiring locale information in environment information of the medical information processing device;
searching, in a look-up table, a value mapped to by the locale information by using the locale information as a key, the value being associated with a character encoding;
presuming a character encoding of the medical information based on a result of the searching; and
decoding the input medical information based on the presumed character encoding.

9. The medical information processing method according to claim 8, further comprising:
determining whether an encoding declaration of the medical information includes a deficit or an inconsistency; and
in response to a determination that the encoding declaration includes the deficit or the inconsistency, receiving input of a user selection concerning whether the presumed character encoding is to be specified in the encoding declaration.

* * * * *